(12) United States Patent
Chinnaiyan et al.

(10) Patent No.: US 8,524,682 B2
(45) Date of Patent: Sep. 3, 2013

(54) COMPOSITIONS AND METHODS FOR INHIBITING EZH2

(75) Inventors: Arul M. Chinnaiyan, Plymouth, MI (US); Sooryanarayana Lnu, Ann Arbor, MI (US); Qi Cao, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 492 days.

(21) Appl. No.: 12/778,739

(22) Filed: May 12, 2010

(65) Prior Publication Data

US 2010/0222420 A1 Sep. 2, 2010

Related U.S. Application Data

(62) Division of application No. 12/167,520, filed on Jul. 3, 2008, now abandoned.

(60) Provisional application No. 60/958,151, filed on Jul. 3, 2007.

(51) Int. Cl.
  *C12N 15/11* (2006.01)
(52) U.S. Cl.
  USPC ........................................ 514/44 A
(58) Field of Classification Search
  USPC ........................................ 514/44 A
  See application file for complete search history.

(56) References Cited

U.S. PATENT DOCUMENTS

| | | | |
|---|---|---|---|
| 4,952,564 A | 8/1990 | Sato | |
| 6,696,407 B1 | 2/2004 | Longo | |
| 2003/0175736 A1 | 9/2003 | Chinnaiyan | |
| 2005/0032882 A1 | 2/2005 | Chen | |
| 2008/0050744 A1* | 2/2008 | Brown et al. | 435/6 |
| 2008/0171715 A1* | 7/2008 | Brown et al. | 514/44 |

FOREIGN PATENT DOCUMENTS

| | | |
|---|---|---|
| WO | WO 03/075943 | 9/2003 |
| WO | WO 2010/034006 A2 * | 3/2010 |

OTHER PUBLICATIONS

Saunders et al. PNAS 104, 3300-3005, 2007.*
Su et al. Cancer Res. 2009, 69:1135-1142.*
Yamazaki, Shoji, et al.; "Isoliquiritigenin suppresses pulmonary metastasis of mouse renal cell carcinoma"; Cancer Letters (2002); vol. 183, pp. 29-30.
Tohtong, R., et al.; "Dependence of metastatic cancer cell invasion on MLCK-catalyzed phosphorylation of myosin regulatory light chain"; Prostate Cancer and Prostatic Diseases (2003); vol. 6, pp. 212-216.
Bachmann, Ingeborg M., et al.; "EZH2 Expression Is Associated With High Proliferation Rate and Aggressive Tumor Subgroups in Cutaneous Melanoma and Cancers of the Endometrium, Prostate, and Breast"; Journal of Clinical Oncology (Jan. 10, 2006); vol. 24, No. 2, pp. 268-273.
Maggiolini M. et al., Estrogenic and antiproliferative activities of isoliquiritigenin in MCF7 breast cancer cells, The Journal of Steroid Biochemistry and Molecular Biology, Nov. 2002, vol. 82, No. 4-5, pp. 315-322.
Raman J.D. et al., Increased expression ofthe polycomb group gene, EZH2, in transitional cell carcinoma of the bladder, Clin. Cancer Res., Dec. 15, 2005, vol. 11, No. 24, pp. 8570-8576.
Dhanasekaran, et al., "Delineation of prognostic biomarkers in prostate cancer" Nature 2001 vol. 412 (6849) pp. 822-826.
Jacobs, et al., "Polycomb repression: from cellular memory to cellular proliferation and cancer" Biochim Biophys Acta 2002;1602(2):151-61.
Jacobs, et al., "Cellular memory of transcriptional states by Polycomb-group proteins" Semin Cell Dev Biol 1999 vol. 10(2) pp. 227-235.
Kanazawa, et al., "Isoliquiritigenin Inhibits the Growth of Prostate Cancer" Eur Urol. May 2003;43(5):580-6.
Kleer, et al., "EZH2 is a marker of aggressive breast cancer and promotes neoplastic transformation of breast epithelial cells" Proc Natl Acad Sci U S A 2003;100(20):11606-11.
Macias, et al., "Bioactive phenolics and polar compounds from Melilotus Messanensis" Phytochemistry (1998) 50(1): 35-46.
Satijn, et al., "Polycomb group protein complexes: do different complexes regulate distinct target genes?" Biochim Biophys Acta (1999) 1447(1):1-16.
Srivastava, et al., "4,4'-Dihydroxychalkone-2'-O-(4-O-β-D-glucopyranosyl)α-L-rhamnopyranoside from *Viburnum cortinifolium*" Indian J. Chem., Sect. B (1981), 20B(4): 347-8.
Tamir, "Estrogen-like activity of glabrene and other constituents isolated from licorice root" Steroid Biochem. Mol. Biol. (2001) 78(3): 291-8.
Varambally, et al., "The polycomb group protein EZH2 is involved in progression of prostate cancer" Nature 2002 vol. 419, (6907):624-9.
Yu, et al., "Vasorelaxant effect of isoliquiritigenin, a novel soluble guanylate cyclase activator, in rat aorta" Brit. J. Pharmacol. 114 (1995), 1587.

* cited by examiner

*Primary Examiner* — Brian Whiteman
(74) *Attorney, Agent, or Firm* — Casimir Jones SC

(57) ABSTRACT

The present invention relates to therapeutic targets for cancer. In particular, the present invention relates to small molecules and nucleic acids that target EZH2 expression in prostate cancer.

4 Claims, 6 Drawing Sheets

Figure 1

|  |  |  | SEQ ID No: |
|---|---|---|---|
| Position 40-66 of EZH2 3' UTR | 5' ...AGCUUCAGGAACCUCG-AGUACUGUG... | 7mer-m8 | 1 |
| hsa-miR-101 | 3'    GAAGUC--AAUAGUGUCAUGACAU |  | 2 |
| Position 87-121 of EZH2 3' UTR | 5' ...GCAGUUUGAAAUUCUGAAUUUGCAAAGUACUGUA... | 8mer | 3 |
| hsa-miR-101 | 3'    GAAGUCAA--------------UAGUGUCAUGACAU |  | 4 |

A

B

SEQUENCE LISTING

<160> NUMBER OF SEQ ID NOS: 4

<210> SEQ ID NO 1
<211> LENGTH: 25
<212> TYPE: RNA
<213> ORGANISM: Homo sapiens

<400> SEQUENCE: 1
agcuucagga accucgagua cugug                                     25

<210> SEQ ID NO 2
<211> LENGTH: 22
<212> TYPE: RNA

```
-continued

<213> ORGANISM: Homo sapiens

<400> SEQUENCE: 2
uacaguacug ugauaacuga ag                                           22

<210> SEQ ID NO 3
<211> LENGTH: 34
<212> TYPE: RNA
<213> ORGANISM: Homo sapiens

<400> SEQUENCE: 3
gcaguuugaa auucugaauu ugcaaaguac ugua                              34

<210> SEQ ID NO 4
<211> LENGTH: 22
<212> TYPE: RNA
<213> ORGANISM: Homo sapiens

<400> SEQUENCE: 4
uacaguacug ugauaacuga ag                                           22
```

COMPOSITIONS AND METHODS FOR INHIBITING EZH2

CROSS REFERENCE TO RELATED APPLICATIONS

This application is a divisional of U.S. patent application Ser. No. 12/167,520, filed: Jul. 3, 2008, which claims priority to U.S. Provisional Patent Application Ser. No. 60/958,151, filed: Jul. 3, 2007, each of which are herein incorporated by reference in their entirety.

STATEMENT REGARDING FEDERALLY SPONSORED RESEARCH OR DEVELOPMENT

This invention was made with government support under grant numbers CA97063, CA69568, and 111274 awarded by the National Institutes of Health and grant number W81XWH-08-0110 awarded by the Army Medical Research and Material Command. The government has certain rights in the invention.

FIELD OF THE INVENTION

The present invention relates to therapeutic targets for cancer. In particular, the present invention relates to small molecules and nucleic acids that target EZH2 expression in cancer (e.g., prostate cancer and other solid tumors).

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166:402 [2001]). Thus, development of new therapeutic targets and agents is needed.

SUMMARY OF THE INVENTION

The present invention relates to therapeutic targets for cancer. In particular, the present invention relates to small molecules and nucleic acids that target EZH2 expression in cancer (e.g., prostate cancer and other solid tumors).

For example, in some embodiments, the present invention provides a method of inhibiting the growth of cells, comprising contacting a cell expressing EZH2 with a miRNA under conditions such that the expression of EZH2 in the cell is inhibited. In some embodiments, the miRNA is miR-101. In some embodiments, the cell is a cancer cell. In some embodiments, the cell is in an organism (e.g., an animal or an animal diagnosed with cancer (e.g., prostate, breast, or bladder cancer)).

In other embodiments, the present invention provides a method of inhibiting the growth of cells, comprising contacting a cell expressing EZH2 with a small molecule compound under conditions such that the expression of EZH2 in the cell is inhibited. In some embodiments, the small molecule is isoliquiritigenin or related compounds or the compounds described in Tables 1 and 2. In some embodiments, the cell is a cancer cell. In some embodiments, the cell is in an organism (e.g., an animal or an animal diagnosed with cancer (e.g., prostate, breast, or bladder cancer)).

DESCRIPTION OF THE FIGURES

FIG. 1 shows the sequence database entry for mir-101 from Sanger's Registry. The cartoon depicts the predicted stem-loop hairpin. miR-101 is predicted to target the 3' UTR of EZH2 at 2 independent sites and both predictions are the top ranked hits from the Sanger Registry.

DEFINITIONS

Figure 2:
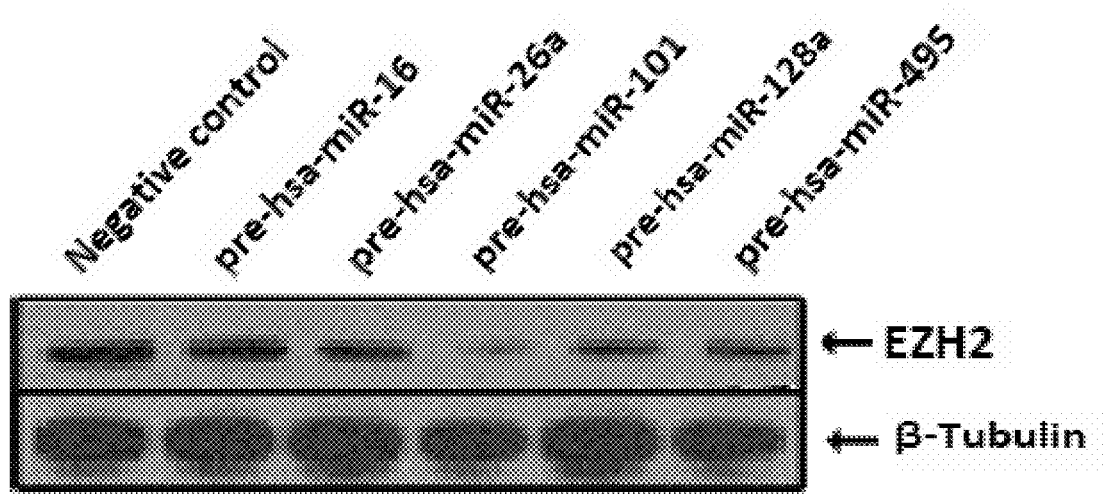
FIG. 2 shows that miR-101 down regulates EZH2. Immunoblot analysis of the breast cancer cell line SKBr3 transfected with precursor miR-101 or controls and non-EZH2 targeting precursor miR's as well as other EZH2 targeting predicted miR's with low scores.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. In some embodiments, cancer marker genes serve as targets for anticancer therapeutics.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other. When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." As used herein, the term "$T_m$" is used in reference to the "melting temperature."

The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\%\ G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "chemical moiety" refers to any chemical compound containing at least one carbon atom. Examples of chemical moieties include, but are not limited to, aromatic chemical moieties, chemical moieties comprising Sulfur, chemical moieties comprising Nitrogen, hydrophilic chemical moieties, and hydrophobic chemical moieties.

As used herein, the term "aliphatic" represents the groups including, but not limited to, alkyl, alkenyl, alkynyl, alicyclic.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, —NH$_2$, —NHCOCH$_3$, —OH, lower alkoxy (C$_1$-C$_4$), halo (—F, —Cl, —Br, or —I).

As used herein, the term "substituted aliphatic," refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—CH$_3$), or aryl groups.

As used herein, the term "substituted heterocyclic" refers to a heterocylic structure where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein, the term "a moiety that participates in hydrogen bonding" or "a chemical moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups ($C_1$-$C_4$) to which the respective oxygen-containing functional group is attached. Thus, for example, the term "lower carbonyl" refers to inter alia, formaldehyde, acetaldehyde. Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present invention can be the π electrons of an aromatic ring.

The term "derivative" of a compound, as used herein, refers to a chemically modified compound wherein the chemical modification takes place either at a functional group of the compound (e.g., aromatic ring) or benzodiazepine backbone. Such derivatives include, but are not limited to, esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

DETAILED DESCRIPTION OF THE INVENTION

The present invention relates to therapeutic targets for cancer. In particular, the present invention relates to small molecules and nucleic acids that target EZH2 expression in cancer (e.g., prostate cancer and other solid tumors).

I. EZH2 Targeted Cancer Therapies

In some embodiments, the present invention provides therapies for cancer (e.g., prostate cancer and other solid tumors). In some embodiments, therapies target EZH2.

The Enhancer of Zeste Homolog 2 (EZH2) was identified as a cancer marker with altered expression in cancer (e.g. prostate cancer) in previous studies (e.g., U.S. Patent application 2003-0175736 A1; herein incorporated by reference in its entirety). EZH2 belongs to the Polycomb group protein family (PcG). The polycomb group proteins help in maintaining cellular identity by transcriptional repression of target genes (Jacobs et al., Semin Cell Dev Biol 1999; 10(2):227-35; Jacobs et al., Biochim Biophys Acta 2002; 1602(2):151-61.). DNA microarrays identified EZH2 as being up-regulated in hormone-refractory metastatic prostate cancer (Dhanasekaran et al., Nature 2001; 412(6849):822-6; Varambally et al., Nature 2002; 419(6907):624-9). EZH2 is upregulated in aggressive breast tumors and is a mediator of a pro-invasive phenotype (Kleer et al., Proc Natl Acad Sci USA 2003; 100(20):11606-11). Overexpression of EZH2 in immortalized human mammary epithelial cell lines promotes anchorage-independent growth and cell invasion (Kleer et al., supra). EZH2-mediated cell invasion required an intact SET domain and histone deacetylase activity. Previous studies provided evidence for a functional link between dysregulated EZH2 expression, transcriptional repression, and neoplastic transformation (Varambally et al., supra; Kleer et al, supra).

The present invention is not limited to a particular mechanism. Indeed, an understanding of the mechanism is not necessary to understand the present invention. Nonetheless, based upon previous studies on Polycomb group proteins, several models have been hypothesized to explain how PcG proteins exert their function. They are: 1) inhibition of the transcriptional machinery and alteration of the transcriptional state of cells; 2) forming a complex to prevent chromatin from binding to other proteins; and 3) recruiting target genes to repressive nuclear structures (Satijn et al., Biochim Biophys Acta 1999; 1447(1):1-16). Previous studies indicated EZH2 upregulation in breast cancer and that EZH2 mediates invasion (Kleer et al., supra).

Metastatic prostate disease almost universally overexpresses EZH2. Furthermore, aggressive localized tumors of the prostate, bladder, and breast and other solid tumors also express high levels of EZH2. Accordingly, it is contemplated that anti EZH2 therapies find use in the treatment of cancer, in particular metastatic cancers such as prostate, breast and bladder cancer.

A. miRNA Therapies

In some embodiments, the present invention provides MicroRNAs that inhibit the expression of EZH2. MicroRNAs are regulatory, non-protein-coding, endogenous RNAs that have recently gained considerable attention in the scientific community. They are 18-24 nucleotides in length and are thought to regulate gene expression through translational repression by binding to a target mRNA (Lim et al., Science 2003; 299(5612):1540; Chen et al., Semin Immunol 2005; 17(2):155-65; Sevignani et al., Mamm Genome 2006; 17(3): 189-202). They are also proposed to regulate gene expression by mRNA cleavage, and mRNA decay initiated by miRNA-guided rapid deadenylation (Wu et al., Proc Natl Acad Sci USA 2006; 103(11):4034-9). miRNAs are abundant, highly conserved molecules and predicted to regulate a large number of transcripts. To date the international miRNA Registry database has more than 600 human identified microRNAs (Griffiths-Jones et al., Nucleic Acids Res 2006; 34 (Database issue):D140-4) and their total number in humans has been predicted to be as high as 1,000 (Berezikov et al., Cell 2005; 120(1):21-4). Many of these microRNAs exhibit tissue-specific expression (Sood et al., Proc Natl Acad Sci USA 2006; 103(8):2746-51) and many are defined to be either tumor suppressors or oncogenes (Lee et al., Curr Opin Investig Drugs 2006; 7(6):560-4; Zhang et al., Dev Biol 2006; Calin et al., Nat Rev Cancer 2006; 6(11):857-66) and play a crucial role in variety of cellular processes such as cell cycle control, apoptosis, and haematopoiesis. Dysregulation of several miRNAs are thought to play a significant role in human disease processes including tumorigenesis (Hwang et al., Br J Cancer 2006; 94(6):776-80; Thomson et al., Genes Dev 2006; 20(16):2202-7).

Several microRNAs are located in the region of hot spots for chromosomal abnormalities (Calin et al., Oncogene 2006; 25(46):6202-10; Calin et al., Proc Natl Acad Sci USA 2004; 101(9):2999-3004). This results in abnormal expression of miRNAs which affect cellular functions. Recent studies indicate that selected miRNAs may play a role in human cancer pathogenesis. For example, deletions or mutations in genes that code for miRNA tumor suppressors lead to loss of a miRNA or miRNA cluster, and thereby contribute to oncogene deregulation (Zhang et al., supra; Calin et al., supra). The results of large-scale miRNA profiling studies using normal and cancer tissues show that a number of microRNAs are either overexpressed or downregulated in tumors (Alvarez-Garcia et al., Development 2005; 132(21):4653-62; Volinia et al., Proc Natl Acad Sci USA 2006; 103(7):2257-61; Cummins et al., Proc Natl Acad Sci USA 2006; 103(10):3687-92; Yanaihara et al., Cancer Cell 2006; 9(3):189-98; Iorio et al., Cancer Res 2005; 65(16):7065-70; Calin et al., Proc Natl Acad Sci USA 2004; 101(32):11755-60; Calin et al., N Engl J Med 2005; 353(17):1793-801; Pallante et al., Endocr Relat Cancer 2006; 13(2):497-508). It has been shown that miRNA genes are frequently located in cancer-associated genomic regions or fragile sites (Calin et al., Proc Natl Acad Sci USA 2004; 101(9):2999-3004). The genes encoding mir-15 and mir-16 are located at chromosome 13q14, a region that is deleted in the majority of B-cell chronic lymphocytic leukemias (B-CLL) indicating that mir-15 and mir-16 may function as tumor suppressors. let-7 miRNA family members are known to down regulate the oncogene RAS (Johnson et al., Cell 2005; 120(5):635-47). Its expression is reduced in tumors which in turn contributes to the elevated activity of the RAS pathway (Yanaihara et al., Cancer Cell 2006; 9(3):189-98). Expression levels of miR-143 and miR-145 were decreased in colon cancer tissues as well as in cancer cell lines (Michael et al., Mol Cancer Res 2003; 1(12):882-91). In contrast, several microRNAs are upregulated in cancer. Members of the miR-17 cluster provide an oncogenic function via their upregulated expression by c-Myc leading to effects on downstream genes which are mediators of cell cycle and apoptosis events (O'Donnell et al., Nature 2005; 435(7043):839-43).

Many microRNAs play a role during development and tissue differentiation (Pasquinelli et al., Curr Opin Genet Dev 2005; 15(2):200-5). miR-181, a microRNA that is strongly upregulated during differentiation, participates in establishing the muscle phenotype. Recent studies suggest that miR-181 down regulates the homeobox protein Hox-A11 (Naguibneva et al., Nat Cell Biol 2006; 8(3):278-84). Similarly miR-196 is involved in regulating HOXB8 confirming the significant roles played by microRNA during developmental processes. A recent study from Lim et al., (Yekta et al., Science 2004; 304(5670):594-6) showed that a few microRNAs can regulate large numbers of target mRNA and their studies also indicated that the miRNA can downregulate not only the proteins, but the transcript level of the target mRNA. Specific expression of microRNA are of prognostic significance, indicating that miRNAs are determinants of clinical aggressiveness (Volinia et al., supra, Iorio et al. Cancer Res 2005; 65(16):7065-70; Lu et al., Nature 2005; 435(7043):834-8). Thus, microRNA expression profiles can serve as a new class of cancer biomarkers. Breast cancer microRNA profiling studies by Iorio et al., (supra) indicated the expression patterns of several microRNAs were significantly different between normal and neoplastic tissues. This profiling study indicated miR-21 and miR-155 to be consistently up regulated and miR-10b, miR-125b and miR-145 to be down regulated. Further, breast tumor microRNA profiling distinguished normal from malignant breast tissue and correlated with breast cancer histopathologic features such as tumor size, nodal involvement, proliferative capacity and vascular invasiveness.

During experiments conducted during the course of development of embodiments of the present invention a search of the miRNA Registry database for microRNA that would target EZH2 indicated has-miR-101. Further experiments conducted during the course of development of embodiments of the present invention demonstrated that EZH2 expression is inhibited by miR-101.

Accordingly, in some embodiments, the present invention provides methods of inhibiting EZH2 expression and/or activity using microRNAs (e.g., miR-101). In some embodiments, miRNAs inhibit the expression of EZH2 protein. In other embodiments, miRNAs inhibit EZH2 activity (e.g., cell invasion activity).

The present invention is not limited to miR-101. Additional miRNAs can be screened for their activity against EZH2 using any suitable method, including, but not limited to, those disclosed in Example 1 below.

Suitable nucleic acids for use in the methods described herein include, but are not limited to, pri-miRNA, pre-miRNA, mature miRNA or fragments of variants thereof that retain the biological activity of the miRNA and DNA encoding a pri-miRNA, pre-miRNA, mature miRNA, fragments or variants thereof, or DNA encoding regulatory elements of the miRNA.

In some embodiments the nucleic acid encoding the disclosed inhibitory nucleic acids, for example an miRNA molecule, is on a vector. These vectors include a sequence encoding a mature microRNA and in vivo expression elements. In a preferred embodiment, these vectors include a sequence encoding a pre-miRNA and in vivo expression elements such that the pre-miRNA is expressed and processed in vivo into a mature miRNA. In other embodiments, these vectors include a sequence encoding the pri-miRNA gene and in vivo expression elements. In this embodiment, the primary transcript is first processed to produce the stem-loop precursor miRNA molecule. The stem-loop precursor is then processed to produce the mature microRNA. Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV4O-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA.

Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murray, E. J. Ed. "Methods in Molecular Biology," vol. 7, Humana Press, Inc., Cliffton, N.J. (1991).

In some embodiments, vectors comprise in vivo expression elements, which are any regulatory nucleotide sequence, such as a promoter sequence or promoter-enhancer combination, which facilitates the efficient expression of the nucleic acid to produce the microRNA. The in vivo expression element may, for example, be a mammalian or viral promoter, such as a constitutive or inducible promoter or a tissue specific promoter, examples of which are well known to one of ordinary skill in the art. Constitutive mammalian promoters include polymerase promoters as well as the promoters for the following genes: hypoxanthine phosphoribosyl transferase (HPTR), adenosine dearninase, pyruvate kinase, and beta.-actin. Exemplary viral promoters which function constitutively in eukaryotic cells include promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include, but are not limited to, HMG-COA reductase promoter, sterol regulatory element 1, phosphoenol pyruvate carboxy kinase (PEPCK) promoter, human C-reactive protein (CRP) promoter, human glucokinase promoter, cholesterol 7-alpha hydroylase (CYP-7) promoter, beta-galactosidase alpha-2,6 sialyltransferase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include the uteroglobin promoter. Exemplary tissue-specific expression elements for adrenal cells include cholesterol side-chain cleavage (SCC) promoter. Exemplary tissue-specific expression elements for the general nervous system include gamma-gamma enolase (neuron-specific enolase, NSE) promoter. Exemplary tissue-specific expression elements for the brain include the neurofilament heavy chain (NF-H) promoter. Exemplary tissue-specific expression elements for lymphocytes include the human CGL-1/granzyme B promoter, the terminal deoxy transferase (TdT), lambda 5, VpreB, and ick (lymphocyte specific tyrosine protein kinase p56lck) promoter, the human CD2 promoter and its 3' transcriptional enhancer, and the human NK and T cell specific activation (NKG5) promoter. Exemplary tissue-specific expression elements for the colon include pp 60c-src tyrosine kinase promoter, organ-specific neoantigens (OSNs) promoter, and colon specific antigen-P promoter. Exemplary tissue-specific expression elements for breast cells include the human alpha-lactalbumin promoter. Exemplary tissue-specific expression elements for the lung include the cystic fibrosis transmembrane conductance regulator (CFTR) gene promoter. Other elements aiding specificity of expression in a tissue of interest can include secretion leader sequences, enhancers, nuclear localization signals, endosmolytic peptides, etc. Preferably, these elements are derived from the tissue of interest to aid specificity.

In general, the in vivo expression element includes, as necessary, 5' non-transcribing and 5' non-translating sequences involved with the initiation of transcription. They optionally include enhancer sequences or upstream activator sequences.

The miRNA can be isolated from cells or tissues, recombinantly produced, or synthesized in vitro by a variety of techniques well known to one of ordinary skill in the art. In one embodiment, miRNA is isolated from cells or tissues.

Techniques for isolating miRNA from cells or tissues are well known to one of ordinary skill in the art. For example, miRNA can be isolated from total RNA using the mirVana miRNA isolation kit from Ambion, Inc. Another techniques utilizes the flashIPAGE™ Fractionator System (Ambion, Inc.) for PAGE purification of small nucleic acids.

The miRNA can be obtained by preparing a recombinant version thereof (e.g., by using the techniques of genetic engineering to produce a recombinant nucleic acid which can then be isolated or purified by techniques well known to one of ordinary skill in the art). This embodiment involves growing a culture of host cells in a suitable culture medium, and purifying the miRNA from the cells or the culture in which the cells are grown. For example, the methods include a process for producing a miRNA in which a host cell containing a suitable expression vector that includes a nucleic acid encoding an miRNA is cultured under conditions that allow expression of the encoded miRINA. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE, dextran mediated transfection, or electroporation (Davis, L. et al., Basic Methods in Molecular Biology (1986)).

Any host/vector system can be used to express one or more of the miRNAs. These include eukaryotic hosts such as HeLa cells and yeast, as well as prokaryotic hosts such as *E. coli* and *B. subtilis*. miRNA can be expressed in mammalian cells, yeast, bacteria, or other cells where the miRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In some embodiments, the miRNA is expressed in mammalian cells. Examples of mammalian expression systems include C 127, monkey COS cells, Chinese Hamster Ovary (CHO) cells, human kidney 293 cells, human epidermal A43 1 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. In some embodiments, mammalian expression vectors will comprise an origin of replication, a suitable promoter, polyadenylation site, transcriptional termination sequences, and 5' flanking non-transcribed sequences. DNA sequences derived from the SV4O viral genome, for example, SV4O origin, early promoter, enhancer, splice, and polyadenylation sites may be used to provide the required nontranscribed genetic elements.

Suitable yeast strains include, but are not limited to, *Saccharomyces cerevisiae, Schizosaccharomyces pombe, Kiuyveromyces* strains, *Gandida*, or any yeast strain capable of expressing miRNA. Suitable bacterial strains include, but are not limited to, *Escherichia coli, Bacillus subtilis, Salmonella typhiinurium*, or any bacterial strain capable of expressing miRNA.

In a preferred embodiment, genomic DNA encoding a mi-RNA is isolated, the genomic DNA is expressed in a mammalian expression system, and RNA is purified and modified as necessary for administration to an individual. In some embodiments the mi-RNA is in the form of a pre-miRNA, which can be modified as desired (i.e. for increased stability or cellular uptake).

Knowledge of DNA sequences of miRNA allows for modification of cells to permit or increase expression of an endogenous miRNA. Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter is inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems, each of which is herein incorporated by reference. Cells also may be engineered to express an endogenous gene comprising the miRNA under the control of inducible regulatory elements, in which case the regulatory sequences of the endogenous gene may be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al., each of which is herein incorporated by reference.

The miRNA may be prepared by culturing transformed host cells under culture conditions suitable to express the miRNA. The resulting expressed miRNA may then be purified from such culture (i.e., from culture medium or cell extracts) using known purification processes, such as gel filtration and ion exchange chromatography. The purification of the miRNA may also include an affinity column containing agents which will bind to the protein; one or more column steps over such affinity resins as concanavalin A-agarose, HEPARINTOYOPEARL or Cibacrom blue 3GA SEPHAROSE; one or more steps involving hydrophobic interaction chromatography using such resins as phenyl ether, butyl ether, or propyl ether; immunoaffinity chromatography, or complementary cDNA affinity chromatography.

The miRNA may also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science 244:1288-1292 (1989)), such that the animals express the miRNA. Transgenic animals, preferably non-human mammals, are produced using methods as described in U.S. Pat. No. 5,489,743 to Robinson, et al., and PCT Publication No. WO 94/28 122 by Ontario Cancer Institute, each of which is herein incorporated by reference. miRNA can be isolated from cells or tissue isolated from transgenic animals as discussed above.

In some embodiments, the miRNA can be obtained synthetically, for example, by chemically synthesizing a nucleic acid by any method of synthesis known to the skilled artisan. The synthesized miRNA can then be purified by any method known in the art. Methods for chemical synthesis of nucleic acids include in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle, herein incorporated by reference in its entirety).

In some circumstances, for example, where increased nuclease stability is desired, nucleic acids having nucleic acid analogs and/or modified internucleoside linkages are utilized. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH$_2$—S—CH$_2$), dimethylene-sulfoxide (—CH$_2$—SO—CH$_2$), dimethylene-sulfone (—CH$_2$—SO$_2$—CH$_2$), 2'-O-alkyl, and 2'-deoxy-2'-fluoro phosphorothioate internucleoside linkages are well known in the art (see Uhlmam et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al., U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmaeker, et al., U.S. Pat. No. 5,610,289 to Cook, et al. and U.S. Pat. No. 5,858,988 to Wang, each of which is herein incorporated by reference in its entirety, also describe nucleic acid analogs for enhanced nuclease stability and cellular uptake. Additional methods for the administrations of miRNAs can be found, for example, in US20050261218A1, US20060105360A1, WO06119365A2, and WO05078096A2, each of which is herein incorporated by reference in its entirety.

The compounds can be administered to a host in an amount effective to treat or inhibit cancer or tumor growth (e.g., prostate cancer). The compositions are administered to an individual in need of treatment or prophylaxis of at least one symptom or manifestation (since disease can occur/progress in the absence of symptoms) of cancer. In some embodiments, the compositions are administered in an effective amount to inhibit gene expression of EZH2.

B. Small Molecule Therapies

In other embodiments, the present invention provides small molecule inhibitors of EZH2 expression or activity. Experiments conducted during the course of development of embodiments of the present invention utilized cDNA expression microarray analysis using the RNA isolated from EZH2 overexpressing cells along with control RNA. The expression microarray of the present invention is also suitable for use in high-throughput experiments.

It was observed that the tumor suppressor protein E-cadherin was specifically downregulated in EZH2 overexpressing cells. These observations were further confirmed by immunoblot assays as well as co-immunostainings. Furthermore, the inverse correlation between increased EZH2 expression and E-cadherin down regulation was observed in aggressive breast tumors as well.

Further experiments conducted during the course of development of embodiments of the present invention identified isoliquiritigenin as an inhibitor of EZH2 expression. Accordingly, in some embodiments, the present invention provides methods of treating cancer (e.g., metastatic cancer) using isoliquiritigenin or related compounds.

Isoliquiritigenin, one of the components in the root of *Glycyrrhiza glabra* L., is a member of the flavonoids, which are known to have an anti-tumor activity in vitro and in vivo. (Kanazawa et al., Eur Urol. 2003 May; 43(5):580-6.). Isoliquiritigenin has also been shown to be a soluble guanylate cyclase activator (Yu et al., Brit. J. Pharmacol. 114 (1995), 1587) and to possess estrogen-like activity (see, for example, S. Tamir, J: Steroid Biochem. Mol. Biol. (2001), 78(3): 291-8). Isoliquiritigenin has been shown to activate estrogen receptor-alpha and -beta and trigger biochemical reactions in cancer cells. The COX-2 inhibitory activity of isoliquiritigenin has also been demonstrated. (See e.g., WO 03/075943; U.S. Pat. Nos. 6,696,407; and 4,952,564, each of which is herein incorporated by reference).

As used herein, isoliquiritigenin refers to CAS Reg. No. 961-29-5; also known as 2',J,d'-trihydroxychalcone, a pharmaceutically acceptable salt or ester of isoliquiritigenin, a selectively substituted analog of isoliquiritigenin, an extract of *Glycyrrhiza uralersis* 5 or *Glycyrrhiza glabra*, or a combination comprising one or more of the foregoing compounds. An ester of isoliquiritigenin is preferably a glycoside of isoliquiritigenin.

There is no particular limit on the monosacharide or polysaccharide used to form the glycoside of isoliquiritigenin. Suitable monosaccharides sugars include, for example, glucose, glucuronic acid, mannose, fructose, galactose, xylose, rutinose, rhamnose, and the like, and combinations comprising one or more of the foregoing monosaccharides. Suitable polysaccharides include, for example, dimers, trimers, oligomers, and polymers formed from one or more of the above monosaccharides.

An isoliquiritigenin analog includes, for example, phloretin, 2',4,4' trihydroxychalcone, or the like, or a combination comprising one or more of the foregoing isoliquiritigenin analogs.

Methods for synthesizing or isolating isoliquiritigenin, its pharmaceutically acceptable salts or esters, its selectively substituted analogs, are known in the art. See, for example, S. K. Srivastava et al., Indian J. Chem., Sect. B (1981), 20B(4): 347-8; Macias et al., Phytochemistry (1998), 50(1): 35-46, each of which is herein incorporated by reference.

In some embodiments, when isoliquiritigenin is present, the isoliquiritigenin comprises greater than or equal to 0.5 weight percent, more preferably greater than or equal to about 1 weight percent, still more preferably greater than or equal to about 2 weight percent, even more preferably greater than or equal to about 5 weight percent, even more preferably greater than or equal to about 10 weight percent, still more preferably greater than or equal to about 20 weight percent of the total weight of the composition.

In some embodiments, the cancer is prostate. In other embodiments, the cancer is bladder, breast, or other solid tumors. Additional small molecule EZH2 inhibitors are identified, for example, using the compositions and methods of the present invention. The present invention additionally contemplates mimetics, analogs and modified forms of isoliquiritigenin.

The present invention is not limited to a particular mechanism. Indeed, an understanding of the mechanism is not necessary to practice the present invention. Nonetheless, it is contemplated that a small molecule inhibitor against EZH2 finds use in the treatment of metastatic disease, which almost universally overexpresses EZH2. Furthermore, aggressive localized tumors of the prostate, bladder, and breast and other solid tumors expressing high levels of EZH2 are also therapeutically targeted by EZH2 inhibitors (e.g., isoliquiritigenin).

Additional small molecule inhibitors were identified using a screening assaying. Exemplary compounds are shown in Tables 1 and 2. In some embodiments, these compounds find use in the inhibition of EZH2 (e.g., as cancer therapeutics), alone or in combination with additional therapeutic agents described herein.

C. Pharmaceutical Compositions

The compounds are preferably employed for therapeutic uses in combination with a suitable pharmaceutical carrier. Such compositions comprise an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are described herein.

For the use of miRNA therapeutics, it is understood by one of ordinary skill in the art that nucleic acids administered in vivo are taken up and distributed to cells and tissues (Huang, et al., FEBS Lett. 558(1-3):69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, Nature, 385:721-725 (1997). Small nucleic acids are readily taken up into T24 bladder carcinoma tissue culture cells (Ma, et al., Antisense Nucleic Acid Drug Dev. 8:415-426 (1998). siRNAs have been used for therapeutic silencing of an endogenous genes by systemic administration (Soutschek, et al., Nature 432, 173-178 (2004)).

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or micro spheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example in Sambrook et al., 1989, Molecular Cloning: A Laboratory Manual, Cold Spring Harbor Laboratory, New York; and Ausubel et al., 1994, Current Protocols in Molecular Biology, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. By way of example, and not by limitation, the nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative. The compositions may take such forms as.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. For administration by inhalation, the compounds are conveniently delivered in the form of an aerosol spray presentation from pressurized packs or a nebulizer, with the use of a suitable propellant.

In some embodiments, the compound described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the compounds are conjugated to lipophilic groups like cholesterol and laurie and lithocholic acid derivatives with C32 functionality to improve cellular uptake. For example, cholesterol has been demonstrated to enhance uptake and serum stability of siRNA in vitro Lorenz, et al., Bioorg. Med. Chem. Lett. 14(19):4975-4977 (2004)) and in vivo (Soutschek, et al., Nature 432(7014):173-178 (2004)). In addition, it has been shown that binding of steroid conjugated oligonucleotides to different lipoproteins in the bloodstream, such as LDL, protect integrity and facilitate biodistribution (Rump, et al., Biochem. Pharmacol. 59 (11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe (II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines.

U.S. Pat. No. 6,919,208 to Levy, et al., herein incorporated by reference, also described methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

The formulations described herein of the nucleic acids embrace fusions of the nucleic acids or modifications of the nucleic acids, wherein the nucleic acid is fused to another moiety or moieties, e.g., targeting moiety or another therapeutic agent. Such analogs may exhibit improved properties such as activity and/or stability. Examples of moieties which may be linked or unlinked to the nucleic acid include, for example, targeting moieties which provide for the delivery of nucleic acid to specific cells, e.g., antibodies to pancreatic cells, immune cells, lung cells or any other preferred cell type, as well as receptor and ligands expressed on the preferred cell type. Preferably, the moieties target cancer or tumor cells. For example, since cancer cells have increased consumption of glucose, the nucleic acids can be linked to glucose molecules. Monoclonal humanized antibodies that target cancer or tumor cells are preferred moieties and can be linked or unlinked to the nucleic acids. In the case of cancer therapeutics, the target antigen is typically a protein that is unique and/or essential to the tumor cells (e.g., the receptor protein HBR-2).

In general, methods of administering compounds, including nucleic acids, are well known in the art. In particular, the routes of administration already in use for nucleic acid therapeutics, along with formulations in current use, provide preferred routes of administration and formulation for the nucleic acids described above.

Compositions can be administered by a number of routes including, but not limited to: oral, intravenous, intraperitoneal, intramuscular, transdermal, subcutaneous, topical, sublingual, or rectal means. Compounds can also be administered via liposomes. Such administration routes and appropriate formulations are generally known to those of skill in the art.

Administration of the formulations described herein may be accomplished by any acceptable method which allows the compounds, for example miRNA or nucleic acid encoding the miRNA, to reach its target.

The particular mode selected will depend of course, upon factors such as the particular formulation, the severity of the state of the subject being treated, and the dosage required for therapeutic efficacy. As generally used herein, an "effective amount" is that amount which is able to treat one or more symptoms of age related disorder, reverse the progression of one or more symptoms of age related disorder, halt the progression of one or more symptoms of age related disorder, or prevent the occurrence of one or more symptoms of age related disorder in a subject to whom the formulation is administered, as compared to a matched subject not receiving the compound.

The actual effective amounts of compound can vary according to the specific compound or combination thereof being utilized, the particular composition formulated, the mode of administration, and the age, weight, condition of the individual, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. The composition can be injected intraderinally for treatment or prevention of age related disorder, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The nucleic acid may be delivered in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these.

Microcapsules of the foregoing polymers containing nucleic acids are described in, for example, U.S. Pat. No. 5,075,109, herein incorporated by reference. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the miRNA is contained in a formulation within a matrix (for example, as described in U.S. Pat. Nos. 4,452,775, 4,675,189, 5,736,152, 4,667,013, 4,748,034 and 5,239,660, herein incorporated by reference), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition penneates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the miRNA employed and the condition of the individual, as well as the body weight or surface area of the individual to be treated. The size of the dose is also determined by the existence, nature, and extent of any adverse side-effects that accompany the administration of a particular vector, formulation, or the like in a particular individual.

Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the individual. Administration can be accomplished via single or divided doses.

In vitro models can be used to determine the effective doses of the nucleic acids as a potential age related disorder treatment, as described in the examples. In determining the effective amount of the compound to be administered in the treatment or prophylaxis of disease the physician evaluates circulating plasma levels, formulation toxicities, and progression of the disease. For nucleic acids, the dose administered to a 70 kilogram individual is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-age-related disorder cocktail.

Certain embodiments of the invention provide pharmaceutical compositions containing (a) one or more nucleic acid or small molecule compounds and (b) one or more other chemotherapeutic agents. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

II. Antibodies

The present invention provides isolated antibodies. In some embodiments, the present invention provides monoclonal antibodies that specifically bind to an isolated polypeptide comprised of at least five amino acid residues of EZH2. These antibodies find use in the therapeutic and drug screening methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

EXPERIMENTAL

The following examples are provided in order to demonstrate and further illustrate certain preferred embodiments and aspects of the present invention and are not to be construed as limiting the scope thereof.

Example 1 miRNA Inhibition of EZH2 Expression

A. Experimental Approach

The primary structure of precursor miR-101 is shown in FIG. 1. FIG. 1 shows the sequence database entry for mir-101 from Sanger's Registry. The cartoon depicts the predicted stem-loop hairpin. miR-101 is predicted to target the 3' UTR of EZH2 at 2 independent sites and both predictions are the top ranked hits from the Sanger Registry.

The functional consequences of perturbing miR-101 levels in cells was evaluated. Expression of EZH2 protein was measured by immunoblot analysis. Invasion assays were carried out as previously described (Kleer et al., supra) and pre-miR-101 was transfected along with siRNA against EZH2 (as a positive control) and luciferase siRNA (as a negative control) as well as several unrelated miRs.

B. Results

It was assessed whether miR-101 regulates EZH2 expression in cell lines. Upon transfection of the precursor miR-101 in SKBr3 breast cancer cells a marked decrease in EZH2 protein expression was observed (FIG. 2). Control miR5 and other miR5 predicted to regulate EZH2 with high scores (as per the Sanger Registry) did not decrease EZH2 protein levels.

Figure 3:
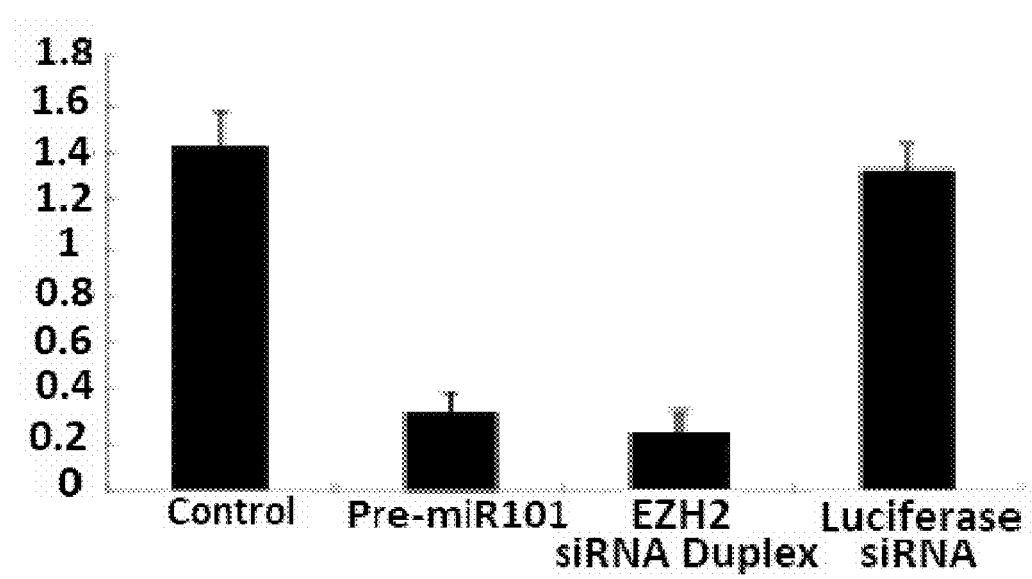
FIG. 3 shows that miR-101 inhibits invasion. SKBr3 cells were transfected with either control miR, miR-101 which targets EZH2, siRNA duplex against EZH2 or luciferase duplex. A reconstituted basement membrane invasion chamber assay (Chemicon) was used to assess invasion.

To assess the functional relevance of miR-101 relative to EZH2 function a cell invasion assay was utilized. Previous studies have shown that knock-down of EZH2 in cancer cell lines expressing high levels of EZH2 abrogates cell invasion (FIG. 3). Over-expression of miR-101 in SKBr3 cells induced marked reduction of cell invasion by knocking down EZH2 protein levels. Thus microRNA 101 serves as a therapeutic for knocking down EZH2 in aggressive tumors which overexpress EZH2.

Example 2

Small Molecule Inhibition of EZH2

Figure 4:
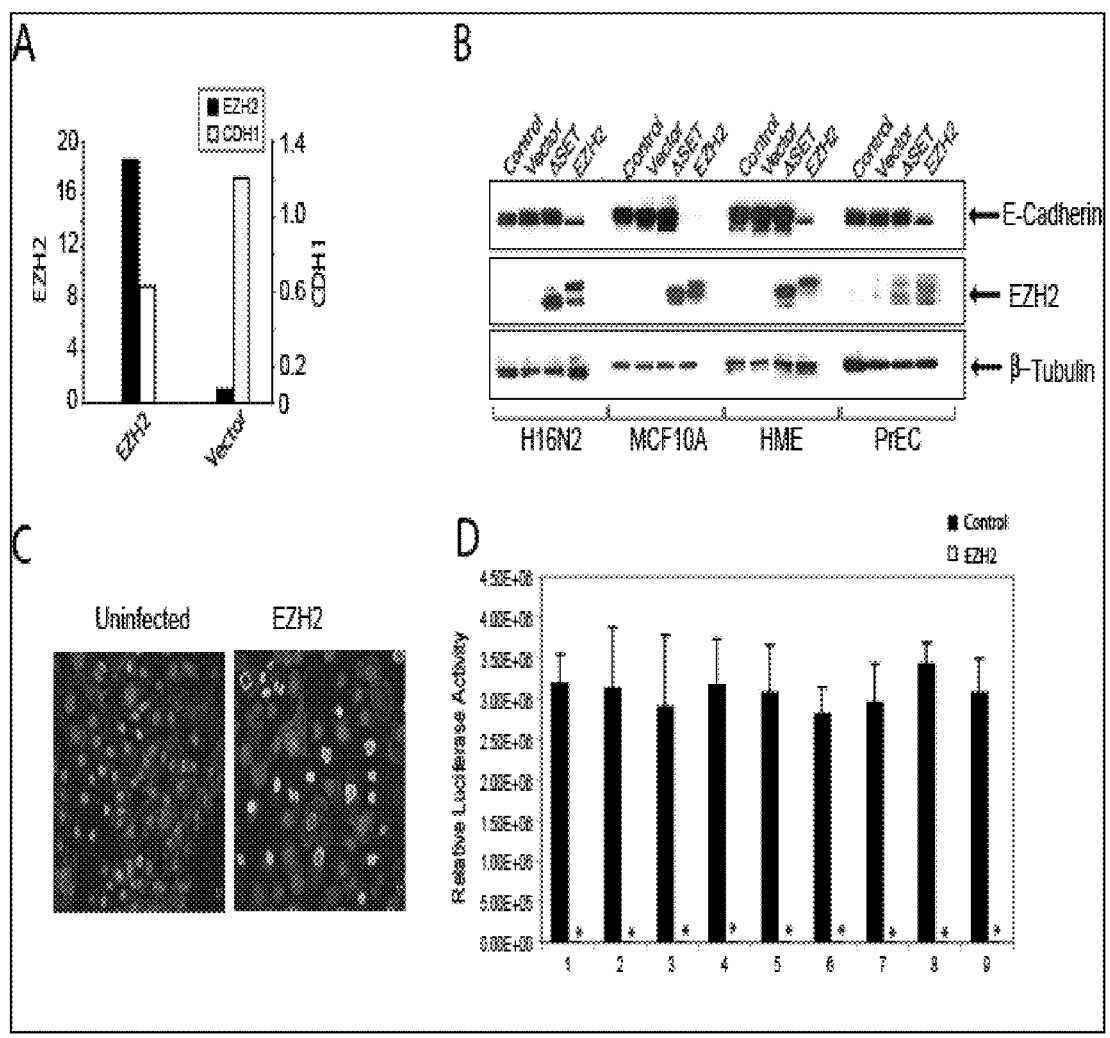
FIG. 4 shows that EZH2 mediates down regulation of E-cadherin (CDH1). A, Histogram of E-cadherin expression from expression profiling experiment using RNA from EZH2 overexpressing breast cells and vector control. B, Immunoblot analysis of EZH2 and E-cadherin using the lysates from the breast cell line H16N2, MCF10A, HME and primary prostate cell PrEC infected with adenovirus encoding EZH2, EZH2 SET mutant, control virus infected cells using EZH2 and E-cadherin antibody. β-Tubulin was included as a loading control. C, Co-immunostaining and confocal imaging of breast cell line H16N2 infected with EZH2. Panel on the right is uninfected cells and panel on the right EZH2 overexpressing cells. D, Adaptation of E-cadherin promoter-luciferase reporter assay for high throughput screening assay (96 well format). Asterisk (*) highlights the significant down regulation of luciferase activity in EZH2 overexpressing cells.

In order to understand the mechanism of EZH2 mediated invasion, cDNA expression microarray analysis was performed using the RNA isolated from EZH2 overexpressing cells along with control RNA (FIG. 4A). It was observed that the tumor suppressor protein E-cadherin was specifically downregulated. These observations were further confirmed by immunoblot assays as well as coimmunostainings (FIG. 4 B, C). Furthermore, the inverse correlation between increased EZH2 expression and E-cadherin down regulation was observed in aggressive breast tumors as well. The studies showed that the oncogenic function of EZH2 works by activating a pro-invasion program through transcriptional repression of E-cadherin among other factors.

A. Experimental Approach

A high throughput screening protocol was used to identify small molecule inhibitors of EZH2. Primary breast cancer cells were transfected with the E-cadherin promoter luciferase reporter gene and infected with the EZH2 adenovirus to suppress luciferase expression 48 hours prior to compound addition. Eighteen hours prior to compound addition, cells were trypsinized and distributed into 384-well plates in 60 μl of medium using the Multidrop equipment. At time zero, compounds were transferred from 1.5 mM DMSO stocks to the cell plates in a final compound concentration of about 5 μM. This concentration was chosen based on other cell-based assays in which higher concentrations caused substantial cell toxicity and did not yield significantly more "hits". After 24 hours, the expressed luciferase activity was measured by adding 50 μl of the medium and 10 μl of Steady-Glo luciferase reagent (Promega). Sample plates were read in the Pherastar plate reader (BMG Labtech). Each plate in the screen contains 320 compounds to be tested plus 64 control wells placed in the outer two columns on each side of the plate (>50,000 compounds are screened). The "Positive" control was EZH2 adenovirus infected cells followed by treatment with the HDAC inhibitor SAHA (500 nM) which shows the activity expected in the presence of an inhibitor. More than 4000 small molecules were screened, which included synthetic chemicals as well as natural products that are available in the Center for Chemical Genomics (CCG) library at the University of Michigan.

B. Results

The E-cadherin promoter-luciferase reporter construct was utilized in a high throughput screening assay using a chemical library. Initial screens indicated the utility of the gain of function assay with a good Z'-score. Isoliquiritigenin (FIG. 5A) was identified as a potent small molecule inhibitor of EZH2 activity.

Figure 5:
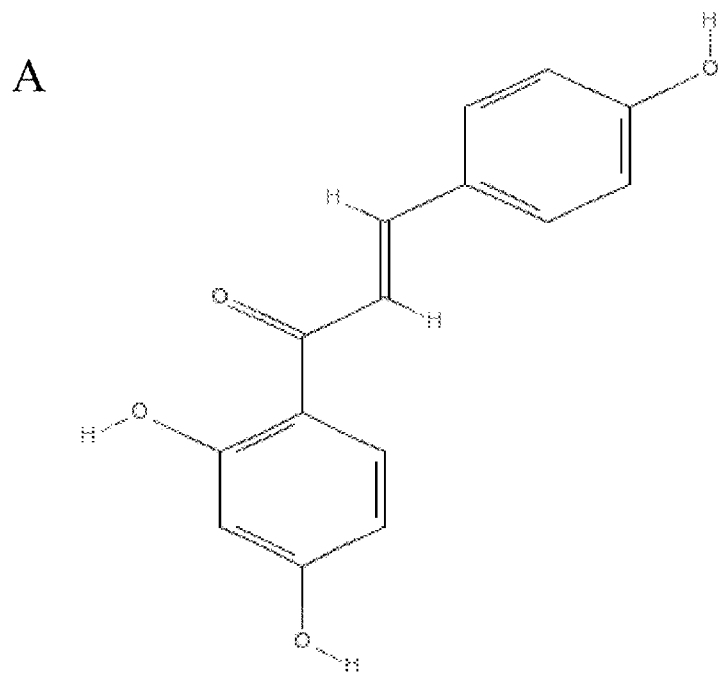
FIG. 5 shows that isoliquiritigenin inhibits EZH2 mediated gene repression. A, Chemical structure of the flavonoid isoliquiritigenin. B, Quantitative SYBR green RT-PCR of EZH2 and E cadherin transcripts in cell lines over expressing EZH2 and control adenoviruses. RT-PCR on each sample was performed in duplicate, and a ratio was calculated relative to the housekeeping genes GAPDH. Transcripts were also measured in cells that were treated with isoliquiritigenin or other small molecules.
Figure 5:
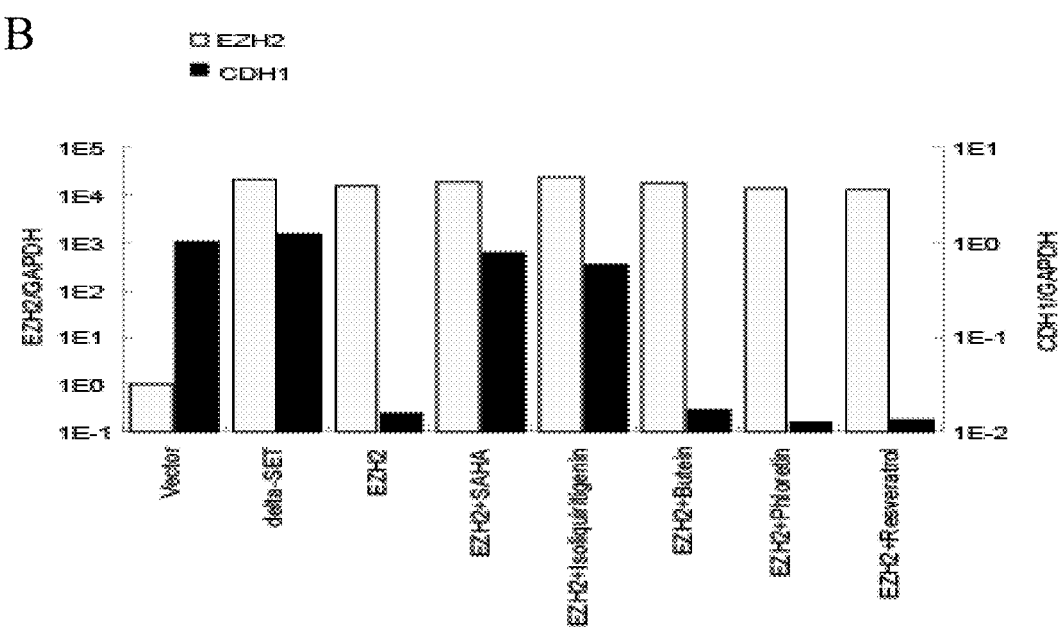
Figure 6:
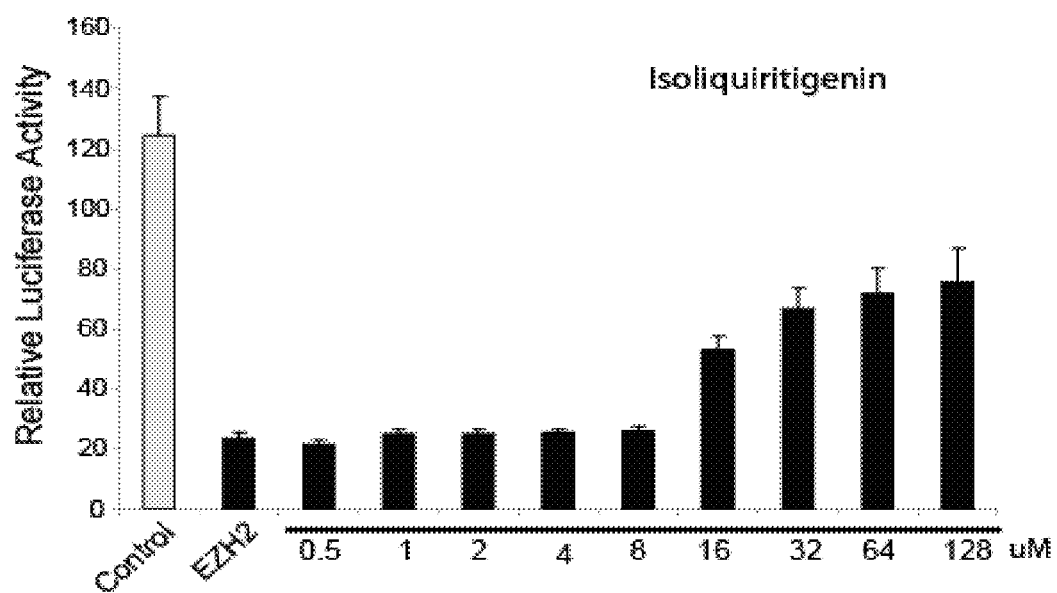
FIG. 6 shows that isoliquiritigenin inhibits EZH2 activity. A, Dose response of isoliquiritigenin on inhibiting EZH2 mediated repression. B, A reconstituted basement membrane invasion chamber assay was used to assess the invasion of breast epithelial cell line infected with EZH2 and control adenoviruses as well as SET domain mutant EZH2 adenovirus. EZH2 treated cells were also treated with SAHA, the HDAC inhibitor and isoliquiritigenin, the small molecule inhibitor of EZH2 and the control small molecule phloretin.
Figure 6:
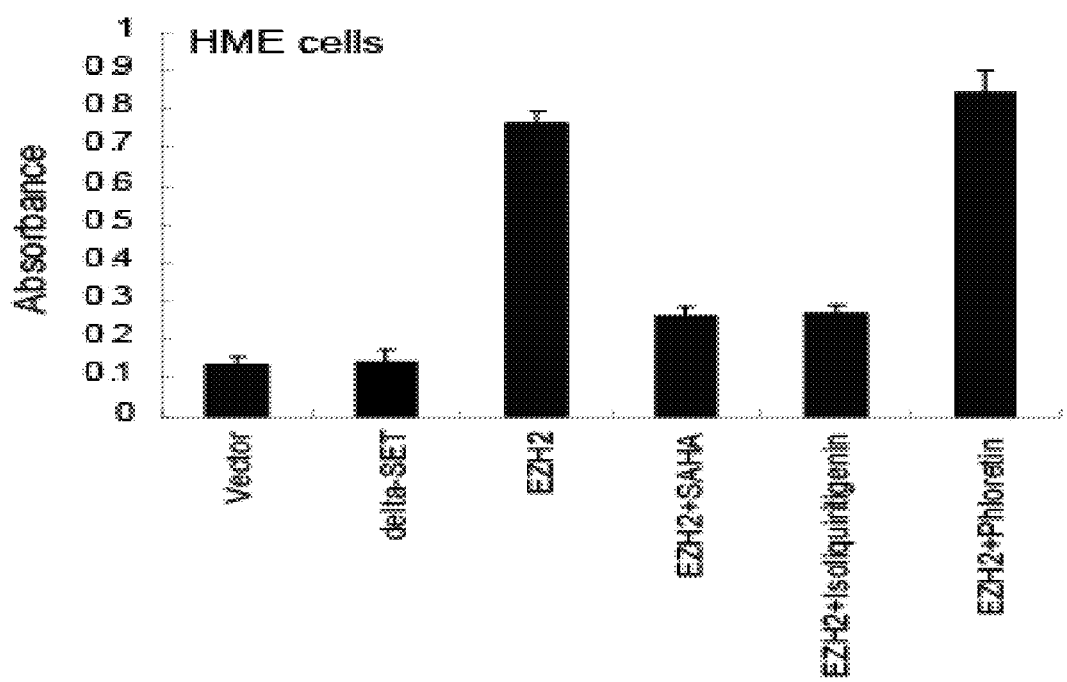

The effect of this small molecule inhibitor on inhibiting the gene repression mediated by EZH2 was further analyzed. As shown in FIG. 5B, isoliquiritigenin was able to significantly inhibit the EZH2 mediated E cadherin repression. Evaluation of the dose response indicated that 16 μM isoliquiritigenin could optimally inhibit the EZH2 mediated E cadherin repression (FIG. 6A).

Further studies confirmed the utility of this plant flavonoid in inhibiting the EZH2 activity in cancer cell invasion. While the breast cell line HME acquires invasive potential upon EZH2 overexpression, addition of isoliquiritigenin inhibited this invasion. A control small molecule with similar structure did not inhibit the invasion mediated by EZH2 overexpression demonstrating the specificity of isoliquiritigenin in inhibiting the EZH2 activity (FIG. 6B).

The preliminary screen was extended to 70,000 compounds. Table 1 below shows a list of compounds identified as having EZH2 inhibitory activity. Table 2 shows 33 compounds selected as candidates for dose response screens as well as secondary screens such as invasion, apoptosis, and xenograft models.

TABLE 1

EZH2 Inhibitors
EZH2 Inhibitor- IUPAC name

1-{[4-amino-5-(2,2-dimethylpropanoyl)-1,3-thiazol-2-yl]sulfanyl}-3,3-dimethylbutan-2-one
4-[4-(4-methyl-1,3-thiazol-2-yl)phenyl]-1,2,3-thiadiazole
2-{[(3,4-dichlorophenyl)carbamoyl]amino}benzoic acid
N-(2-methylquinolin-6-yl)quinoxaline-2-carboxamide
2-[(4-tert-butylphenyl)carbonyl]-1H-imidazole
1-(2-hydroxyphenyl)-3-[4-(methoxymethoxy)phenyl]propane-1,3-dione
N-(3-acetylphenyl)-8-methoxy-2-oxo-2H-chromene-3-carboxamide
1-{3-[4-(2-phenylethynyl)phenyl]-1H-pyrazol-1-yl}ethan-1-one
3-(thiophen-2-yl)benzoic acid
5-(6-methoxynaphthalen-2-yl)-1H-pyrazole
4-methyl-5-[3-(methylsulfanyl)-1H-pyrazol-5-yl]-2-(thiophen-2-yl)-1,3-thiazole
2-{[(2-chloro-6-fluorophenyl)methyl]sulfanyl}-1-(2,3-dihydro-1,4-benzodioxin-6-yl)ethan-1-one
3-(3-chlorophenyl)-5-(thiophen-3-yl)-1,2,4-oxadiazole
2,3-dihydro-1-benzofuran-5-ylmethanimidamido thiophene-2-carboxylate
N-(2,3-dihydro-1,4-benzodioxin-6-yl)[(furan-2-ylmethyl)carbamothioyl]formamide
N-[4-(diethylamino)phenyl]-3-methylbenzamide
3-[5-(1,2-oxazol-3-yl)thiophen-2-yl]-5-phenyl-1,2,4-oxadiazole TABLE 1-continued EZH2 Inhibitors
EZH2 Inhibitor- IUPAC name ethyl (2E)-2-cyano-3-{[(E)-{[4-(dimethylamino)phenyl]methylidene}amino](methane)sulfinimidamido}prop-2-enoate
(2Z)-2-(4-ethylphenyl)-3-(4-methoxyphenyl)prop-2-enenitrile
5-tert-butyl-3-methyl-N-phenylthieno[3,2-b]thiophene-2-carboxamide
5-(1-butyl-2-oxo-2,3-dihydro-1H-indol-3-ylidene)-2-(piperidin-1-yl)-4,5-dihydro-1,3-thiazol-4-one
(2E,6E)-2,6-bis(thiophen-2-ylmethylidene)cyclohexan-1-one
2-[(E)-2-(3,4-dimethoxyphenyl)ethenyl]-1,3-benzothiazole
2-chloro-N-[3-hydroxy-4-(5-methyl-1,3-benzoxazol-2-yl)phenyl]-5-nitrobenzamide
6-chloro-2-phenyl-4H-thiochromen-4-one
methyl 2-(3,4-dihydro-2H-1,5-benzodioxepine-7-amido)benzoate
3-chloro-N,N-dimethyl-4-[(1E)-2-[2-(quinoxalin-2-yl)hydrazin-1-ylidene]methyl]aniline
(2E)-1-(2-methyl-1H-indol-3-yl)-3-(thiophen-2-yl)prop-2-en-1-one
N-(2,3-dihydro-1,4-benzodioxin-6-yl)-2-(thiophen-2-yl)-1,3-thiazole-4-carboxamide
4-[(E)-2-(1-methyl-1H-1,3-benzodiazol-2-yl)ethenyl]-1,3-thiazole
3-(4-bromophenyl)-3,4-dihydro-1,2,3-benzotriazin-4-one
N-(2,4-dichlorophenyl)-3,4-dihydro-2H-1-benzopyran-2-carboxamide
N,N-dimethyl-4-[(E)-2-phenylethenyl]aniline
2-(3,4-dichlorophenyl)quinoxaline
N-(3-tert-butyl-1H-pyrazol-5-yl)-2,3-dihydro-1,4-benzodioxine-2-carboxamide
(2E)-2-(1,3-benzothiazol-2-yl)-3-(4-chlorophenyl)prop-2-enenitrile
(4-tert-butylphenyl)methanimidamido 2-(thiophen-2-yl)acetate
5-[4-(3-methyl-1-benzothiophen-2-yl)-1,3-thiazol-2-yl]-1,2-oxazole
1-(4-fluorophenyl)-3-(1-phenyl-5-propyl-1H-pyrazol-4-yl)urea
2-[(2Z)-2-phenyl-2-[(2E)-2-(thiophen-2-ylmethylidene)hydrazin-1-ylidene]ethyl]-1H-1,3-benzodiazole
N-{7-oxo-8-oxa-4-thiatricyclo[7.4.0.0^{2,6}]trideca-1(9),2,5,10,12-pentaen-5-yl}thiophene-2-carboxamide
2-(2-chlorophenyl)-1-[4-(dimethylamino)phenyl]ethan-1-one
ethyl 4-cyano-1-(4-methylphenyl)-1H-pyrazole-3-carboxylate
3-hydrazinylquinoxaline-2-thiol
1-[(5-tert-butylthiophen-2-yl)carbonyl]piperidine
3-[5-(2-phenylethynyl)thiophen-2-yl]-1-(thiophen-2-ylcarbonyl)-1H-pyrazole
2,5-dichloro-N-(2,3-dihydro-1,4-benzodioxin-2-ylmethyl)thiophene-3-carboxamide
1-tert-butyl-N-(2,3-dihydro-1,4-benzodioxin-6-yl)-5-methyl-1H-pyrazole-3-carboxamide
4-(5-propylpyridin-2-yl)benzonitrile
5-(4-chlorophenyl)-3-(2,2-dichloroacetamido)thiophene-2-carboxamide
(4-methanesulfonamidophenyl)methanimidamido thiophene-2-carboxylate
ethyl 7-methyl-2-phenylpyrazolo[1,5-a]pyrimidine-6-carboxylate
6-(4-chlorophenyl)-3-phenylthieno[2,3-e][1,2,4]triazine
1-{1-phenyl-1H-pyrazolo[3,4-d]pyrimidin-4-yl}-2,3-dihydro-1H-indole
5-(4-chlorophenyl)-2-(4-methylphenyl)-2H-1,2,3,4-tetrazole
4-[(1E)-2-(3,5-dichloropyridin-4-yl)hydrazin-1-ylidene]methyl]-N,N-dimethylaniline
3-(5-tert-butyl-1,2-oxazol-3-yl)-1-phenylurea
(4-chlorophenyl)methanimidamido 3-chlorothiophene-2-carboxylate
N-{4-[(E)-2-phenyldiazen-1-yl]phenyl}acetamide
methyl 4-[(pyrimidin-2-ylsulfanyl)methyl]benzoate
2-phenylimidazo[1,2-a]pyridine
6-chloro-2-phenyl-4H-thiochromen-4-one
2-{[(4-methylphenyl)methyl]sulfanyl}-5-(pyrazin-2-yl)-1,3,4-thiadiazole
5,7-dihydroxy-2-(4-hydroxyphenyl)-4H-chromen-4-one
(E)-[1-(1H-pyrrol-2-yl)ethylidene]amino N-(4-chlorophenyl)carbamate
1-benzoyl-3-2,3-dihydro-1H-inden-5-ylthiourea
1-{1-phenyl-1H-pyrazolo[3,4-d]pyrimidin-4-yl}-2,3-dihydro-1H-indole
N,5-diphenyl-1,3,4-oxadiazole-2-carboxamide
(3Z)-3-(2,3-dihydro-1-benzofuran-5-ylmethylidene)-2,3-dihydro-1H-indol-2-one
[(3-methylbutyl)sulfanyl]-N-phenylformamide
2,4-dihydroxy-5,7-diphenylpyrano[2,3-d]pyrimidin-8-ium perchlorate
ethyl 7-hydroxy-9-oxo-9H-xanthene-2-carboxylate
(E)-[(1-tert-butyl-3,5-dimethyl-1H-pyrazol-4-yl)methylidene]amino N-[3-(trifluoromethyl)phenyl]carbamate
5-[(4-iodophenyl)amino]-3-phenyl-1,3-thiazolidine-2,4-dione
N-(furan-2-ylmethyl)-2-[methane(4-phenoxyphenyl)sulfonamido]acetamide
N-(3-methoxyphenyl)-6-phenylpyridazin-3-amine
ethyl (2E)-3-[(2-chlorophenyl)amino]-2-cyanoprop-2-enoate
1-[(3-chloro-1-benzothiophen-2-yl)carbonyl]-1H,2H,3H,4H,6H,10bH-pyrimido[2,1-a]isoindol-6-one
2-(4-chlorophenyl)-5-[(cyclopropylmethyl)sulfanyl]-1,3,4-oxadiazole
1-[6-(benzyloxy)-3-tert-butyl-2-hydroxyphenyl]ethan-1-one
3-[(1E)-1-[(2,2-dichloroethenyl)imino]-2,2-dimethylpropyl]-1-(4-methylphenyl)thiourea
6,7-dimethyl-2-phenylquinoxaline
5-(2,3-dihydro-1-benzofuran-5-yl)-3-(4-fluorophenyl)-1,2,4-oxadiazole
2-{4-[(4-methylphenyl)methoxy]phenyl}acetonitrile
1-cyclohexyl-3-8-oxatricyclo[7.4.0.0^{2,7}]trideca-1(9),2(7),3,5,10,12-hexaen-5-ylurea
5-(1,2,3-thiadiazol-4-yl)-3-[4-(trifluoromethyl)phenyl]-1,2,4-oxadiazole
N-(2-methylquinolin-6-yl)-2-phenylacetamide
3-(piperidin-1-ylcarbonyl)-5-(thiophen-2-yl)-1,2-oxazole
N-(3,4-dimethylphenyl)[(E)-N'-(thiophen-2-ylmethylidene)hydrazinecarbonyl]formamide
2-(2,3-dimethoxyphenyl)-2,3-dihydro-1,3-benzothiazole
2-methyl-5-(naphthalen-2-yl)-1,3-thiazole hydrobromide
(cyclohexylcarbamothioyl)-N-(4-fluorophenyl)formamide
4-(1,3-benzothiazol-2-yl)-1-methyl-1H-pyrazol-3-amine
(4-tert-butylphenyl)methanimidamido 5-methyl-1,2-oxazole-3-carboxylate TABLE 1-continued EZH2 Inhibitors
EZH2 Inhibitor- IUPAC name N-[2-(methylsulfanyl)-1,3-benzothiazol-6-yl]thiophene-2-carboxamide
N-(5-cyclopropyl-1,3,4-thiadiazol-2-yl)-2H-1,3-benzodioxole-5-carboxamide
(2E)-3-(2-chlorophenyl)-N-(2-methylbut-3-yn-2-yl)prop-2-enamide
1-naphthalen-1-yl-3-8-oxatricyclo[7.4.0.0^{2,7}]trideca-1(13),2,4,6,9,11-hexaen-5-ylthiourea
3-methyl-N-phenyl-1-benzothiophene-2-carbothioamide
5-(2,5-dichlorophenyl)-N-[2-(trifluoromethyl)phenyl]furan-2-carboxamide
3-(5-methyl-1,2-oxazol-3-yl)-5-(thiophen-2-yl)-1,2,4-oxadiazole
N-(1H-indazol-3-yl)-3-methoxybenzamide
2-(4-tert-butylphenyl)-5-[(propane-1-sulfonyl)methyl]-1,3,4-oxadiazole
1-[2-(4-chlorophenoxymethyl)-4-methyl-1,3-thiazol-5-yl]ethan-1-one
(4-methanesulfonamidophenyl)methanimidamido N-(4-methylphenyl)carbamate
N-phenyl-4,5,6,7-tetrahydro-1,3-benzothiazol-2-amine hydrochloride
7-nitro-N-(2-phenylethyl)-1H-indole-2-carboxamide
2-{[(2E)-4-(pyridin-2-ylsulfanyl)but-2-en-1-yl]sulfanyl}pyridine
4-[(E)-2-(3-methylthiophen-2-yl)ethenyl]-2-[(3-nitropyridin-2-yl)sulfanyl]pyrimidine
4-(4-chlorophenyl)-2-[(4-methoxyphenyl)methyl]-1,3-thiazole
(3Z)-3-{[5-(thiophen-2-yl)thiophen-2-yl]methylidene}-2,3-dihydro-1H-indol-2-one
N-(4-bromo-2,5-difluorophenyl)-2,3-dimethylbenzamide
sodium N-phenyl(phenylamino)carboximidate
2-(benzylsulfanyl)-N-(2,3-dihydro-1H-inden-2-yl)acetamide
(5Z)-5-[(5-methylfuran-2-yl)methylidene]-3-phenyl-1,3-thiazolidine-2,4-dione
N-{4-[(3-chlorophenyl)carbamoyl]phenyl}thiophene-2-carboxamide
N-[(3-chlorophenyl)methyl]-5-(methylsulfanyl)-1,3,4-thiadiazol-2-amine
(E)-2-(phenylamino)-3-(phenylimino)guanidine
(2Z)-3-methyl-2-[2-(3-methyl-2,3-dihydro-1,3-benzoxazol-2-ylidene)hydrazin-1-ylidene]-2,3-dihydro-1,3-benzoxazole
3-[2-(2H-1,4-benzothiazin-3-yl)hydrazin-1-yl]-2H-1,4-benzothiazine
3-(3,4-dimethyl-1,2-oxazol-5-yl)-1-[4-(dimethylamino)-3,5-difluorophenyl]carbonylurea
(3Z)-3-[2-(2,5-difluorophenyl)hydrazin-1-ylidene]piperidin-2-one
N'-[(E)-[1-(1-benzofuran-2-yl)ethylidene]amino](methylsulfanyl)methanimidamide
(2Z)-3-(9H-fluoren-2-ylcarbamoyl)prop-2-enoic acid
4-[2-(2,3-dihydro-1,4-benzodioxin-6-yl)diazen-1-yl]-N,N-diethylaniline
4,5-dichloro-N-(3-chloro-4-fluorophenyl)-1,2-thiazole-3-carboxamide
5-[4-(4-methoxyphenoxy)phenyl]-1H-pyrazole
1-cyclohexyl-3-[(Z)-(1H-pyrazol-3-ylmethylidene)amino]thiourea
[5-(4-chlorophenyl)-3-methyl-2-sulfanylidene-1,3,4-thiadiazinan-6-ylidene]amino 5-tert-butylthiophene-2-carboxylate
N-(2-phenylethyl)benzenecarbothioamide
5-amino-3-methyl-2-N-phenylthiophene-2,4-dicarboxamide
3-amino-5-(thiophen-3-yl)thiophene-2-carboxamide
(2E)-2-{[4-(trifluoromethoxy)phenyl]imino}-3,4-dihydro-2H-1,3-benzoxazin-4-one
3-hydroxy-9H-xanthen-9-one
4-[(E)-2-(3,5-dihydroxyphenyl)ethenyl]benzene-1,2-diol
(3-chlorophenyl)methanimidamido 6-(2,2,2-trifluoroethoxy)pyridine-3-carboxylate
5-phenyl-3-(pyrrolidin-1-yl)-1,2-thiazole-4-carbonitrile
7-hydroxy-3-(4-hydroxyphenyl)-4H-chromen-4-one
2-(4-fluorophenyl)-2H,3H,5H,6H,7H,8H-[1,2,4]triazolo[4,3-a]pyrimidin-3-one
(4-chlorophenyl)methanimidamido 2,6-difluorobenzoate
2-(2-amino-3-methoxyphenyl)-4H-chromen-4-one
6,7-dimethoxy-2-phenylquinoxaline
6-methoxy-3-phenyl-[1,2,4]triazolo[4,3-a]pyridazine
5-[4-(furan-2-ylcarbonyl)piperazin-1-yl]-3-(thiophen-2-yl)-1,2,4-thiadiazole
(E)-{1-[2-(4-chlorophenoxymethyl)-1,3-thiazol-4-yl]ethylidene}amino benzoate
N-[(2-chloro-6-fluorophenyl)carbonyl]-N'-(4-methylpyridin-2-yl)ethanediamide
(E)-hydroxy[1-(2-phenyl-1,3-thiazol-4-yl)ethylidene]amine
ethyl 1-{[4-(trifluoromethoxy)phenyl]carbamoyl}piperidine-4-carboxylate
3-(3-methyl-1H-indol-1-yl)-N-[4-(morpholin-4-yl)phenyl]propanamide
6,8-dimethyl-1-methylidene-2-(4-methylphenyl)-1,4-dihydronaphthalene
N'-[(2-methyl-1,3-thiazol-4-yl)methoxy]-4-(trifluoromethyl)benzene-1-carboximidamide
1-[4-(benzyloxy)phenyl]-3-[(3-cyanopyridin-2-yl)amino]urea
2-phenylimidazo[1,2-a]pyridine
3-(morpholin-4-yl)-5-[4-(trifluoromethyl)phenyl]-1,2-thiazole-4-carbonitrile
N-(2-chlorophenyl)-2-[(3-cyano-6-acetylpyridin-2-yl)sulfanyl]acetamide
3-[4-(4-methoxyphenyl)-1,3-thiazol-2-yl]-5-methyl-1,2-oxazole
N-(3-bromo-5-methylpyridin-2-yl)-4-ethylbenzamide
2-(5-methyl-1,2-oxazol-3-yl)-5-[3-(trifluoromethyl)phenyl]-1,3,4-oxadiazole
(E)-[1-(3-methyl-1-benzothiophen-2-yl)ethylidene]amino N-phenylcarbamate
N-(2,3-dihydro-1H-inden-2-yl)-3-(3-methyl-1H-indol-1-yl)propanamide
1,3-dimethanesulfonyl-2,3-dihydro-1H-1,3-benzodiazole
methyl 2-[5-methyl-2-(thiophene-2-amido)-1,3-thiazol-4-yl]acetate
4-[(5-{[(4-chlorophenyl)sulfanyl]methyl}furan-2-yl)carbonyl]morpholine
2-oxo-2-phenylethyl 2,3-dimethoxybenzoate
N-(4-chlorophenyl)-4-hydroxy-2-oxo-1,2-dihydroquinoline-3-carboxamide
(2,4-dichlorophenyl)methyl N-[(2-fluorophenyl)carbonyl]carbamate
2-[(4-chlorophenyl)carbonyl]-1-benzofuran
4-chlorophenyl 2,3-dihydro-1-benzofuran-5-carboxylate
2-[4-(dimethylamino)phenyl]-1,2,3,4-tetrahydroquinolin-4-one
[6-(ethylsulfanyl)pyridin-3-yl]methanimidamido thiophene-2-carboxylate

TABLE 1-continued

EZH2 Inhibitors
EZH2 Inhibitor- IUPAC name

Natural extract 1
Natural extract 2

TABLE 2

1) N-(3-acetylphenyl)-8-methoxy-2-oxo-2H-chromene-3-carboxamide
2) 2-chloro-N-[3-hydroxy-4-(5-methyl-1,3-benzoxazol-2-yl)phenyl]-5-nitrobenzamide
3) 5-(1-butyl-2-oxo-2,3-dihydro-1H-indol-3-ylidene)-2-(piperidin-1-yl)-4,5-dihydro-1,3-thiazol-4-one
4) N-(4-fluorophenyl)-N'-(1-phenyl-5-propyl-1H-pyrazol-4-yl)urea
5) 6-(4-chlorophenyl)-3-phenylthieno[2,3-e][1,2,4]triazine
6) N,5-diphenyl-1,3,4-oxadiazole-2-carboxamide
7) ethyl 7-hydroxy-9-oxo-9H-xanthene-2-carboxylate
8) 1-(tert-butyl)-3,5-dimethyl-4-{[({[3-(trifluoromethyl)anilino]carbonyl}oxy)imino]methyl}-1H-pyrazole
9) 2,4-dihydroxy-5,7-diphenylpyrano[2,3-d]pyrimidin-8-iumperchlorate
10) 1-[6-(benzyloxy)-3-(tert-butyl)-2-hydroxyphenyl]ethan-1-one
11) N-(3,4-dimethylphenyl)[(E)-N'-(thiophen-2-ylmethylidene)hydrazinecarbonyl]formamide
12) (2E)-3-(2-chlorophenyl)-N-(2-methylbut-3-yn-2-yl)prop-2-enamide
13) 1-naphthalen-1-yl-3-8-oxatricyclo[7.4.0.0^{2,7}]trideca-1(13),2,4,6,9,11-hexaen-5-ylthiourea
14) 5-(2,5-dichlorophenyl)-N-[2-(trifluoromethyl)phenyl]furan-2-carboxamide
15) 7-nitro-N-phenethyl-1H-indole-2-carboxamide
16) 1,2-di(3-methyl-2,3-dihydro-1,3-benzoxazol-2-yliden)hydrazine
17) N-[4-(dimethylamino)-3,5-difluorobenzoyl]-N'-(3,4-dimethyl-5-isoxazolyl)urea
18) (2Z)-3-(9H-fluoren-2-ylcarbamoyl)prop-2-enoic acid
19) O1-{[6-(2,2,2-trifluoroethoxy)-3-pyridyl]carbonyl}-3-chlorobenzene-1-carbohydroximamide
20) 3-hydroxy-9H-9-xanthenone
21) 6-methoxy-3-phenyl-[1,2,4]triazolo[4,3-a]pyridazine
22) ethyl 1-{[4-(trifluoromethoxy)anilino]carbonyl}-4-piperidinecarboxylate
23) 2-furyl{4-[3-(2-thienyl)-1,2,4-thiadiazol-5-yl]piperazino}methanone
24) 4-[(benzoyloxy)ethanimidoyl]-2-[(4-chlorophenoxy)methyl]-1,3-thiazole
25) 1-[4-(benzyloxy)phenyl]-3-[(3-cyanopyridin-2-yl)amino]urea
26) 3-(morpholin-4-yl)-5-[4-(trifluoromethyl)phenyl]-1,2-thiazole-4-carbonitrile
27) (E)-[1-(3-methyl-1-benzothiophen-2-yl)ethylidene]aminoN-phenylcarbamate
28) 1,3-dimethanesulfonyl-2,3-dihydro-1H-1,3-benzodiazole
29) 2-oxo-2-phenylethyl 2,3-dimethoxybenzoate
30) 4-[(5-{[(4-chlorophenyl)sulfanyl]methyl}furan-2-yl)carbonyl]morpholine
31) (2,4-dichlorophenyl)methylN-[(2-fluorophenyl)carbonyl]carbamate
32) 4-chlorophenyl2,3-dihydro-1-benzofuran-5-carboxylate
33) N-(4-chlorophenyl)-4-hydroxy-2-oxo-1,2-dihydroquinoline-3-carboxamide All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of inhibiting the growth of cells, comprising contacting a cancer cell selected from the group consisting of a prostate cancer cell, a breast cancer cell, and bladder cancer cell overexpressing EZH2 with miR-101 under conditions such that the expression of EZH2 in said cancer cell is inhibited.

2. The method of claim 1, wherein said cell is in an organism.

3. The method of claim 2, wherein said organism is an animal.

4. The method of claim 3, wherein said animal has been diagnosed with cancer.

* * * * *

UNITED STATES PATENT AND TRADEMARK OFFICE
CERTIFICATE OF CORRECTION

PATENT NO.        : 8,524,682 B2
APPLICATION NO.   : 12/778739
DATED             : September 3, 2013
INVENTOR(S)       : Arul Chinnaiyan et al.

It is certified that error appears in the above-identified patent and that said Letters Patent is hereby corrected as shown below:

In the Specification

STATEMENT REGARDING FEDERALLY SPONSORED RESEARCH OR DEVELOPMENT:

Column 1, Lines 13-21, reads: "This invention was made with government support under grant numbers CA97063, CA69568, and 111274 awarded by the National Institutes of Health and grant number W81XWH-08-0110 awarded by the Army Medical Research and Material Command. The government has certain rights in the invention."

HOWEVER, IT SHOULD READ:
"This invention was made with government support under grants CA097063, CA069568, and CA111275 awarded by the National Institutes of Health, and W81XWH-08-1-0110 awarded by the U.S. Army Medical Research and Materiel Command. The government has certain rights in the invention."

Signed and Sealed this
Fourth Day of April, 2017

Michelle K. Lee
*Director of the United States Patent and Trademark Office*